(12) United States Patent
Plaisted et al.

(10) Patent No.: US 7,804,012 B2
(45) Date of Patent: Sep. 28, 2010

(54) INBRED SWEET CORN LINE R605

(75) Inventors: Douglas C. Plaisted, Nampa, ID (US); Stephen Lambert Grier, Stanton, MN (US); Michele L. Gardiner, Nampa, ID (US)

(73) Assignee: Syngenta Participations AG, Basel (CH)

(*) Notice: Subject to any disclaimer, the term of this patent is extended or adjusted under 35 U.S.C. 154(b) by 9 days.

(21) Appl. No.: 12/132,036

(22) Filed: Jun. 3, 2008

(65) Prior Publication Data

US 2009/0019597 A1  Jan. 15, 2009

Related U.S. Application Data

(60) Provisional application No. 60/958,918, filed on Jul. 10, 2007.

(51) Int. Cl.
*A01H 1/00* (2006.01)
*C07H 21/04* (2006.01)
*C07K 14/415* (2006.01)
*C12N 15/00* (2006.01)

(52) U.S. Cl. .............. 800/320.1; 435/468; 435/412; 435/418; 435/424; 530/370; 536/23.1; 800/260; 800/278; 800/303

(58) Field of Classification Search .......... 435/468, 435/412, 418, 424; 530/370; 536/23.1; 800/320.1, 800/260, 278, 303
See application file for complete search history.

(56) References Cited

U.S. PATENT DOCUMENTS

2007/0294791 A1* 12/2007 Plaisted et al. .......... 800/303

\* cited by examiner

*Primary Examiner*—Phuong T Bui
(74) *Attorney, Agent, or Firm*—S. Matthew Edwards

(57) ABSTRACT

An inbred sweet corn line, designated R605, the plants and seeds of inbred sweet corn line R605, methods for producing a maize plant produced by crossing the inbred sweet corn line R605 with itself or with another maize plant, and hybrid maize seeds and plants produced by crossing the inbred sweet corn line R605 with another maize line or plant.

33 Claims, No Drawings

INBRED SWEET CORN LINE R605

FIELD OF THE INVENTION

This invention is in the field of maize breeding, specifically relating to an inbred sweet corn line designated R605.

BACKGROUND OF THE INVENTION

The goal of plant breeding is to combine in a single variety or hybrid various desirable traits. For vegetable crops, such as sweet corn, these traits may include resistance to diseases and insects, tolerance to heat and drought, reducing the time to crop maturity, greater yield, better agronomic quality, processing traits, such as high processing plant recovery, tender kernels, pleasing taste, uniform kernel size and color, attractive husk package and husked ears, ability to ship long distances, ease of mechanical or manual harvest, tipfill, row straight. With mechanical harvesting of many crops, uniformity of plant characteristics such as germination and stand establishment, growth rate, maturity, and plant and ear height, is important.

Sweet corn is a particular type of maize (Zea mays L., often referred to as corn in the United States). Sweet corn is harvested at an earlier maturity than field corn (before it is dry), for a different purpose (usually fresh produce, canning or freezing, for human consumption) and has been bred therefore to be qualitatively and quantitatively different from field corn in a number of respects.

Maize is bred through techniques that take advantage of the plant's method of pollination. A plant is self-pollinated if pollen from one flower is transferred to the same or another flower of the same plant. A plant is cross-pollinated if the pollen comes from a flower on a different plant. Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

A reliable method of controlling male fertility in plants offers the opportunity for improved plant breeding. This is especially true for development of maize hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid maize seed is typically produced by a male sterility system incorporating manual or mechanical detasseling. Alternate strips of two maize inbreds are planted in a field, and the pollen-bearing tassels are removed from one of the inbreds (female). Providing that there is sufficient isolation from sources of foreign maize pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile maize and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach.

The use of male sterile inbreds is but one factor in the production of maize hybrids. The development of maize hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and time consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: F1 to F2; F3 to F4; F4 to F5, etc.

Recurrent selection breeding can be used to improve populations of either self or cross-pollinating crops. Recurrent selection can be used to transfer a specific desirable trait from one inbred or source to an inbred that lacks the trait. This can be accomplished, for example, by first a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred genes, except for the difference made by the transferred gene. As the varieties developed using recurrent selection breeding contain almost all of the characteristics of the recurrent parent, selecting a superior recurrent parent is desirable.

A single cross maize hybrid results from the cross of two inbred lines, each of which has a genotype that complements the genotype of the other. The hybrid progeny of the first generation is designated F1. In the development of commercial hybrids only the F1 hybrid plants are sought. Preferred F1 hybrids are more vigorous than their inbred parents. This hybrid vigor, or heterosis, can be manifested in many polygenic traits, including increased vegetative growth and increased yield.

The development of a maize hybrid involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny (F1). During the inbreeding process in maize, the vigor of the lines decreases. Vigor is restored when two different inbred lines are crossed to produce the hybrid progeny (F1). An important consequence of the homozygosity and homogeneity of the inbred lines is that the hybrid between a defined pair of inbreds will always have the same genotype. Once the inbreds that give a superior hybrid have been identified, the hybrid seed can be reproduced indefinitely as long as the homogeneity of the inbred parents is maintained.

A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). Much of the hybrid vigor exhibited by F1 hybrids is lost in the next generation (F2). Consequently, seed from hybrids is not used for planting stock.

Hybrid seed production requires elimination or inactivation of pollen produced by the female parent. Incomplete removal or inactivation of the pollen provides the potential for self pollination. This inadvertently self pollinated seed may be unintentionally harvested and packaged with hybrid seed. Once the seed is planted, it is possible to identify and select these self pollinated plants. These self pollinated plants will be genetically equivalent to the female inbred line used to produce the hybrid. Typically these self pollinated plants can be identified and selected due to their decreased vigor. Female selfs are identified by their less vigorous appearance for vegetative and/or reproductive characteristics, including shorter plant height, small ear size, ear and kernel shape, cob color, or other characteristics.

Identification of these self pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1-8 (1995), the disclosure of which is expressly incorporated herein by reference. Through these technologies, the homozygosity of the self pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoretica si Aplicata Vol. 20 (1) p. 29-42.

As is readily apparent to one skilled in the art, the foregoing are only two of the various ways by which the inbred can be obtained by those looking to use the germplasm. Other means are available, and the above examples are illustrative only.

Sweet corn is an important and valuable vegetable crop. Thus, a continuing goal of plant breeders is to develop high-yielding hybrids that are agronomically sound based on stable inbred lines. The reasons for this goal are obvious: to maximize the amount of marketable sweet corn produced with the inputs used and minimize susceptibility of the crop to pests and environmental stresses.

To accomplish this goal, the breeder must select and develop superior inbred parental lines for producing hybrids. This requires identification and selection of genetically unique individuals that occur in a segregating population. The segregating population is the result of a combination of cross-over events plus the independent assortment of specific combinations of alleles at many gene loci that results in specific genotypes. The probability of selecting any one individual with a specific genotype from a breeding cross is very low due to the large number of segregating genes and the unlimited recombinations of these genes, some of which may be closely linked. However, the genetic variation among individual progeny of a breeding cross allows for the identification of rare and valuable new genotypes. These new genotypes are neither predictable nor incremental in value, but rather the result of manifested genetic variation combined with selection methods, environments and the actions of the breeder.

Thus, even if the entire genotypes of the parents of the breeding cross were characterized and a desired genotype known, only a few, if any, individuals having the desired genotype may be found in a large segregating F2 population. Typically, however, neither the genotypes of the breeding cross parents nor the desired genotype to be selected is known in any detail. In addition, it is not known how the desired genotype would react with the environment. This genotype by environment interaction is an important, yet unpredictable, factor in plant breeding. A breeder of ordinary skill in the art cannot predict the genotype, how that genotype will interact with various climatic conditions or the resulting phenotypes of the developing lines, except perhaps in a very broad and general fashion. A breeder of ordinary skill in the art would also be unable to recreate the same line twice from the very same original parents as the breeder is unable to direct how the genomes combine or how they will interact with the environmental conditions. This unpredictability results in the expenditure of large amounts of research resources in the development of a superior new maize inbred line, such as a superior new sweet corn inbred line.

SUMMARY OF THE INVENTION

According to the invention, there is provided a novel inbred sweet corn line, designated R605. This invention thus relates to the seeds of inbred sweet corn line R605, to the plants of inbred sweet corn line R605 and parts thereof, for example pollen, ovule, or ear, and to methods for producing a maize plant, preferably a sweet corn plant, by crossing the inbred line R605 with itself or another maize line, preferably a sweet corn line. This invention further relates to hybrid maize seeds, preferably hybrid sweet corn seeds, and plants produced by crossing the inbred line R605 with another maize line, preferably a sweet corn line.

The invention is also directed to inbred sweet corn line R605 into which one or more specific, single gene traits, for example transgenes, have been introgressed from another maize line, such as a field corn line or a sweet corn line, and which has essentially all of the morphological and physiological characteristics of inbred sweet corn line of R605, in addition to the one or more specific, single gene traits introgressed into the inbred. The invention also relates to seeds of an inbred sweet corn line R605 into which one or more specific, single gene traits have been introgressed and to plants of an inbred sweet corn line R605 into which one or more specific, single gene traits have been introgressed. The invention further relates to methods for producing a maize plant, preferably a sweet corn plant, by crossing plants of an inbred sweet corn line R605 into which one or more specific, single gene traits have been introgressed with themselves or with another maize line, such as a field corn line or a sweet corn line. The invention also further relates to hybrid maize seeds, preferably sweet corn seeds, and plants produced by crossing plants of an inbred sweet corn line R605 into which one or more specific, single gene traits have been introgressed with another maize line, such as a field corn line or a sweet corn line. The invention is also directed to a method of producing inbreds comprising planting a collection of hybrid seed, growing plants from the collection, identifying inbreds among the hybrid plants, selecting the inbred plants and controlling their pollination to preserve their homozygosity.

The invention is also directed to a method of producing a sweet corn ear comprising growing a plant according to the instant invention to produce an ear, and harvesting said ear. In one embodiment, the method further comprises isolating a kernel from said ear. In one embodiment, the method further comprises processing said kernel to obtain a sweet corn product. In one embodiment, a sweet corn product according the instant invention is a canned or a frozen product, or a fresh produce.

The invention is also directed to a method of producing a sweet corn product comprising obtaining an ear of a plant according to the instant invention, isolating a kernel from said ear, and processing said kernel to obtain a sweet corn product. In one embodiment, a sweet corn product according the instant invention is a canned or a frozen product, or a fresh produce.

DETAILED DESCRIPTION OF THE INVENTION

According to the invention, there is provided a novel inbred sweet corn line, designated R605. The inbred line R605 has several desirable characteristics including high resistance to most races of *Exserohilum turcicum*, desirable ear appearance, good plant structure and resistance to lodging. It carries the *Puccinia sorghi* (common rust) resistance gene Rp1-I and has resistance to MDMV (Maize Dwarf Mosaic Virus). The rust resistance gene Rp1-I was first described in Hagan, W. L. and A. L. Hooker (1965) Phytopathology 55:193-197. The rust resistance gene Rp1-I was obtained from the publicly available field corn line R168 [10].558, which is a BC10 introgression of the Rp1-I gene into the field corn line R168. Some of the characteristics of inbred sweet corn line R605 are illustrated in Table 1.

Inbred maize lines, such as sweet corn inbred lines, are typically developed for use in the production of hybrid maize lines, for example hybrid sweet corn lines. Inbred maize lines need to be highly homogeneous, homozygous and reproducible to be useful as parents of commercial hybrids. There are many analytical methods available to determine the homozygotic and phenotypic stability of these inbred lines. The oldest and most traditional method of analysis is the observation of phenotypic traits. The data is usually collected in field experiments over the life of the maize plants to be examined. Phenotypic characteristics often observed are for traits associated with plant morphology, ear and kernel morphology, insect and disease resistance, maturity, and yield.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

Some of the most widely used of these laboratory techniques are Isozyme Electrophoresis and RFLPs as discussed in Lee, M., "Inbred Lines of Maize and Their Molecular Markers," The Maize Handbook, (Springer-Verlag, New York, Inc. 1994, at 423-432) incorporated herein by reference. Isozyme Electrophoresis is a useful tool in determining genetic composition, although it has relatively low number of available markers and the low number of allelic variants among maize inbreds. RFLPs have the advantage of revealing an exceptionally high degree of allelic variation in maize and the number of available markers is almost limitless. Maize RFLP linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference. This study used 101 RFLP markers to analyze the patterns of two to three different deposits each of five different inbred lines. The inbred lines had been selfed from nine to 12 times before being adopted into two to three different breeding programs. It was results from these two to three different breeding programs that supplied the different deposits for analysis. These five lines were maintained in the separate breeding programs by selfing or sibbing and rogueing off-type plants for an additional one to eight generations. After the RFLP analysis was completed, it was determined the five lines showed 0-2% residual heterozygosity. Although this was a relatively small study, it can be seen using RFLPs that the lines had been highly homozygous prior to the separate strain maintenance.

The breeding method used was pedigree ear to row. Inbred sweet corn line R605 has shown uniformity and stability within the limits of environmental influence for all the traits as described in the Table 1 that follows. The inbred has been self-pollinated and ear-rowed a sufficient number of generations with careful attention paid to uniformity of plant type to ensure the homozygosity and phenotypic stability necessary to use in commercial production. The line has been increased both by hand and in isolated fields with continued observation for uniformity. No variant traits have been observed or are expected in inbred sweet corn line R605. Inbred sweet corn line R605, being substantially homozygous, can be reproduced by planting seeds of the line, growing the resulting maize plants under self-pollinating or sib-pollinating conditions with adequate isolation, and harvesting the resulting seed, using techniques familiar to the agricultural arts.

The production of maize hybrids, such as sweet corn hybrids, typically comprises planting in pollinating proximity seeds of, for example, inbred sweet corn line R605 and of a different inbred parent maize line, cultivating the seeds of inbred sweet corn line R605 and of said different inbred parent maize plant into plants that bear flowers, emasculating the male flowers of inbred sweet corn line R605 or the male flowers of said different inbred parent maize plant to produce an emasculated plant, allowing cross-pollination to occur between inbred sweet corn line R605 and said different inbred parent maize plant and harvesting seeds produced on said emasculated plant. The harvested seed are grown to produce hybrid maize plants. In one embodiment, inbred sweet corn line R605 is crossed with another inbred sweet corn line to produce hybrid sweet corn seeds. In one embodiment, inbred sweet corn line R605 is crossed with an inbred sweet corn line of the R398-type (see e.g. U.S. Pat. No. 6,034,306, incorporated herein by reference in its entirety) to produce hybrid sweet corn seeds. In several different embodiments, resulting sweet corn hybrid lines are described in Tables 3-15.

TABLE 1

Comparison between Inbred Sweet Corn Line R605 with line Ia5125

| | 605 | | IA5125 | | 605 Compared to IA5125 | |
| --- | --- | --- | --- | --- | --- | --- |
| | mean | std dev | mean | std dev | LSD .05 | Sig Y/N |
| Plant data | | | | | | |
| Plant height (cm) | 165.2 | 23.0 | 157.9 | 14.4 | 9.0 | n |
| Ear height (cm) | 64.7 | 7.3 | 95.8 | 12.2 | 4.7 | y |
| Internode length (cm) | 15.9 | 4.1 | 12.8 | 1.5 | 1.4 | y |
| Number of tillers | 1.1 | 1.2 | 0.5 | 0.6 | 0.4 | y |
| Ears per stalk | 2.025 | 0.480 | 1.3 | 0.4 | 0.2 | y |
| Leaf data | | | | | | |
| Width of ear node leaf (cm) | 7.8 | 1.0 | 8.3 | 0.9 | 0.2 | y |
| Length of ear node leaf (cm) | 67.1 | 4.0 | 83.8 | 8.2 | 0.5 | y |
| Number of leaves above | 5.6 | 0.6 | 6.2 | 0.7 | 3.0 | y |
| Leaf angle (degrees from top of stalk) | 36.4 | 17.1 | 58.6 | 16.6 | 7.9 | y |
| Tassel data | | | | | | |
| Number of primary lateral branches | 12.0 | 2.7 | 34.7 | 4.3 | 1.7 | y |
| Branch angle (degrees from central spike) | 52.1 | 21.3 | 42.3 | 16.3 | 8.9 | y |
| Tassel length (cm) | 33.8 | 3.6 | 26.7 | 2.9 | 1.5 | y |
| Ear data | | | | | | |
| Ear Length (cm) | 14.3 | 1.6 | 11.0 | 2.3 | 1.1 | y |
| Ear diameter (cm) | 3.8 | 0.2 | 4.0 | 0.4 | 0.2 | n |
| Row number | 17.1 | 2.5 | 18.1 | 2.0 | 1.3 | n |
| Kernel Length (mm) | 10.3 | 1.4 | 10.8 | 1.3 | 0.8 | n |
| Kernel width (mm) | 6.6 | 1.7 | 7.3 | 1.0 | 0.8 | n |
| Kernel thickness (mm) | 2.7 | 1.1 | 3.1 | 0.7 | 0.5 | n |
| Percentage of round kernels | 11% | 12.9 | 28.7 | 21.4 | 10.3 | y |
| Weight of 100 kernels(grams) | 9.2 | 1.2 | 18.2 | 3.3 | 1.4 | y |
| Cob diameter (cm) | 2.31 | 0.22 | 2.4 | 0.2 | 0.1 | n |

| | 605 | Ia5125 |
| --- | --- | --- |
| Descriptive ratings | | |
| Leaf sheath pubescence | 9 | 1 |
| Marginal waves | 6 | 2 |
| Longitudinal creases | 5 | 0 |
| Kernel rows | 2 | 2 |
| Row alignment | 1 | 1 |
| Aleurone color pattern | 1 | 1 |
| Endosperm type | sh2 | su |
| Endosperm color | yellow | yellow |
| Anthocyanin of brace roots | 0 | 1 |

TABLE 1-continued

Comparison between Inbred Sweet Corn Line R605 with line Ia5125

Color ratings*

Anther
Glume
Leaf
silk
Husk

*Munsell color guide ratings

In interpreting the foregoing color designations, reference may be had to be made to the Munsell Glossy Book of Color, a standard color reference. Color codes: 1.light green, 2.medium green, 3.dark green, 4.very dark green, 5.green-yellow, 6.pale yellow, 7.yellow, 8.yellow-orange, 9.salmon, 10.pink-orange, 11.pink, 12.light red, 13.cherry red, 14.red, 15.red and white, 16.pale purple, 17.purple, 18.colorless, 19.white, 20.white capped, 21.buff, 22.tan, 23.brown, 24.bronze, 25.variegated, 26.other.

Std Dev=Standard Deviation

Table 1 shows that Inbred sweet corn line R605 differs significantly from line Ia5125 for several traits.

Comparison between Hybrids

TABLE 2

GSS2008

| Trial ID | Admnc | female | male | plant height (ft) | Ear height (in) | Ear Length ave. (in) | row # | Husk length (cm) | Kernel depth (mm) | Tip fill (cm) |
| --- | --- | --- | --- | --- | --- | --- | --- | --- | --- | --- |
| 06SUSNMHTwstNAM1 | N05CXL-9356.9355 | 522 | 605 | 5.5 | | 8 | 16 | 1.5 | | 0.1 |
| 06SPSNMHTBR3NAPL | N05CXL-9356.9355 | 522 | 605 | 4.5 | 30 | 7 | 14.8 | 5 | | 2 |
| 05SUSNMHTNEPNAM1 | 03SFX-325.324 | 522 | 605 | 5.5 | 20 | 7.9 | 16 | 6 | 13 | 0 |
| 06SPSNMHTSG3NAM1 | N05CXL-9356.9355 | 522 | 605 | 5 | 18 | 7.5 | 15.6 | 2 | | 2 |
| 07WNSNMHTCHTCHL1 | N05CXL-9356.9355 | 522 | 605 | | | 7.7 | | 3 | | |
| 06FASNMHTFB2NAPL | 05BXS-3899-1BX/05BXS-3898 | 522 | 605 | 4.5 | | 6.7 | 13 | 4 | | 0.5 |
| 06FASNMHTFB7NAPL | 05BXS-3899-1BX/05BXS-3898 | 522 | 605 | 5.5 | | 6.2 | 16 | 7 | | 4 |
| 06FASNMHTFB8NAPL | 05BXS-3899-1BX/05BXS-3898 | 522 | 605 | 5 | 18 | 7 | | 7 | | 2 |
| 06FASNMHTFB3NAPL | 05BXS-3899-1BX/05BXS-3898 | 522 | 605 | 4.5 | 24 | 7 | | 4 | | 1 |
| 06SPSNMHTB51NAPL | N05CXL-9356.9355 | 522 | 605 | 5 | 18 | 7.4 | 15 | 8 | | 2.5 |
| 06SPSNMHTSG1NAM1 | N05CXL-9356.9355 | 522 | 605 | 5 | 16 | 7.3 | | 5 | | 0.5 |
| 06FASNMHTFB5NAPL | 05BXS-3899-1BX/05BXS-3898 | 522 | 605 | 4.5 | | 6.7 | 14 | 7 | | 1 |
| 06SUSNMHTNMPNAM1 | N05CXL-9356.9355 | 522 | 605 | 6 | 25 | 8.5 | 16 | 1 | 12 | 0 |
| 06FASNMHTFG2NAPL | 05BXS-3899-1BX/05BXS-3898 | 522 | 605 | 6 | | 6.8 | 18 | 3 | | 1 |
| 05SUSSTHTM1FSTAN | 03SFX-325.324 | 522 | 605 | 6.5 | 18 | 8.1 | 16.3 | 1 | 14 | 0.1 |
| 06SPSNMHTFIFID2 | N05CXL-9356.9355 | 522 | 605 | 4 | | 7.7 | 15 | 1.5 | | 0.1 |
| 06SPSNMHTFIFID2 | N05CXL-9356.9355 | 522 | 605 | 4.5 | 12 | 7.8 | 15.2 | 2.5 | | 0.5 |
| 06SPSNMHTB55NAPL | N05CXL-9356.9355 | 522 | 605 | 6.5 | 25 | 7.8 | 15.3 | 6 | | 0.5 |
| 06SPSNMHTB53NAPL | N05CXL-9356.9355 | 522 | 605 | 6.5 | 25 | 7.5 | 15.7 | 6 | | 2 |
| 06SPSNMHTUDENAM1 | N05CXL-9356.9355 | 522 | 605 | | | 8 | 14.7 | 4 | | |
| 06SPSNMHTSG2NAM1 | N05CXL-9356.9355 | 522 | 605 | 6 | 25 | 7.7 | 16.7 | 3 | | 0.5 |
| 06SPSNMHTSG2NAM1 | N05CXL-9356.9355 | 522 | 605 | 6 | 20 | 7.3 | 14.3 | 4 | | 2 |
| 07SPSNMHTB52NAPL | N05CXL-9356.9355 | 522 | 605 | 5.5 | | 7.5 | 14 | 6 | | 1 |
| 05NOSNMHTNMPNAM1 | 03SFX-325.324 | 522 | 605 | 6.3 | 20 | 8.5 | | 1.5 | 12 | 0 |
| 06FASNMHTFG1NAPL | 05BXS-3899-1BX/05BXS-3898 | 522 | 605 | 5.2 | | 7 | 15 | 6 | | 1.5 |
| 07SPSNMHTB51NAPL | N05CXL-9356.9355 | 522 | 605 | 3.5 | | 6.7 | 14 | 5 | | 2.5 |
| | | | mean | 5.3 | 20.9 | 7.4 | 15.3 | 4.2 | 12.8 | 1.1 |
| | | | stdev | 0.8 | 4.6 | 0.6 | 1.1 | 2.1 | 1.0 | 1.0 |

TABLE 3

GSS-5640

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SPSNMHTFIFID2 | 04FXB-420/04FXB-419 | D35332 | 605 | 5 | 14 | 8.3 | 16.5 | 3 | | 0 |
| 05SUSNMHTNEPNAM1 | 04FXB-420/04FXB-419 | D35332 | 605 | 5.6 | 16 | 8 | 17 | 6 | 10 | 0.2 |
| 06FASNMHTFB3NAPL | 04FXB-420/04FXB-419 | D35332 | 605 | 5 | 24 | 7 | | 11 | | 2 |
| 06SUSNMHTNMPNAM1 | 04FXB-420/04FXB-419 | D35332 | 605 | | | 9 | 15.7 | 0 | | 1 |
| 06SPSNMHTSG2NAM1 | 04FXB-420/04FXB-419 | D35332 | 605 | 6.5 | 20 | 7 | 16.8 | 7 | | 1 |
| 05NOSNMHTNMPNAM1 | 04FXB-420/04FXB-419 | D35332 | 605 | 7.5 | 28 | 8.2 | | 2 | 10 | 0 |
| 06SPSNMHTBR3NAPL | 04FXB-420/04FXB-419 | D35332 | 605 | 6 | 28 | 7.5 | 13.6 | 6 | | 2 |
| 05SUSSTHTM1FSTAN | 04FXB-420/04FXB-419 | D35332 | 605 | 6.5 | 20 | 8.1 | 17.3 | 0.5 | 11 | 1.8 |
| | | | mean | 6.0 | 21.4 | 7.9 | 16.2 | 4.4 | 10.3 | 1.0 |
| | | | stdev | 0.9 | 5.5 | 0.7 | 1.4 | 3.7 | 0.6 | 0.9 |

TABLE 4

BSS-4922

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 05NOSNMHTNMPNAM1 | 03NXB-8282.8281 | D35258 | 605 | 6.7 | 24 | 8 | | 1.5 | 12 | 0 |
| 06SPSNMHTBR3NAPL | 05BXS-6240-1BX/05BXS-6239 | D35258 | 605 | 5.5 | 25 | 7 | 16 | 2 | | 0 |
| 06SPSNMHTBR5NAPL | 05BXS-6240-1BX/05BXS-6239 | D35258 | 605 | 5.8 | 23 | 7.3 | 16 | 1 | | 0 |
| 06SPSNMHTSG3NAM1 | 05BXS-6240-1BX/05BXS-6239 | D35258 | 605 | 5.5 | 20 | 7.5 | 18.4 | 5 | | 0.5 |
| 05SUSSTHTM1FSTAN | 03NXB-8282.8281 | D35258 | 605 | 7 | 24 | 8.3 | 17.3 | 0.5 | 11 | 0 |
| 06SPSNMHTSG2NAM1 | 03NXB-8281.8282 | D35258 | 605 | 7 | 28 | 7 | 15.6 | 7 | | 0 |
| 06SPSNMHTFIFID2 | 05BXS-6240-1BX/05BXS-6239 | D35258 | 605 | 5.8 | 18 | 8 | 17.2 | 3 | | 0 |
| 05SUSNMHTNEPNAM1 | 03NXB-8282.8281 | D35258 | 605 | 6.5 | 28 | 8 | 18.3 | 3 | 10 | 0 |
| 05WNSNMHTHMRNAPL | 03NXB-8282.8281 | D35258 | 605 | 3.5 | 12 | 0.5 | | 7 | | 2.5 |
| | | | mean | 5.9 | 22.4 | 6.8 | 17.0 | 3.3 | 11.0 | 0.4 |
| | | | stdev | 1.1 | 5.1 | 2.4 | 1.1 | 2.5 | 1.0 | 0.9 |

TABLE 5

BSS-8040

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SUSNMHTUWLID2 | 05SNX-647/05SNX-646 | C41365 | 605 | 8 | 26 | 8.3 | 18 | 2 | 11 | 0 |
| 06SPSNMHTFIFID2 | 05SNX-647/05SNX-646 | C41365 | 605 | 5.6 | 16 | 8.8 | 18 | 4 | | 0 |
| 06SUSNMHTWQ2NAM1 | 05SNX-647/05SNX-646 | C41365 | 605 | 6.5 | | 9 | 18 | 0.5 | | 0.8 |
| 06SPSNMHTSG2NAM1 | 05SNX-647/05SNX-646 | C41365 | 605 | 7.5 | 32 | 8 | 16.4 | 8 | | 1 |
| 06SPSNMHTBR3NAPL | 05SNX-647/05SNX-646 | C41365 | 605 | 5.4 | 26 | 7.8 | 16.4 | 7 | | 0.2 |
| 05NOSNMHTNMPNAM1 | 05SNX-647/05SNX-646 | C41365 | 605 | | | 8.2 | | 1 | | 0 |
| 06SUSNMHTCS6ID2 | 05SNX-647/05SNX-646 | C41365 | 605 | 8.5 | 30 | 8 | 19.3 | 2.5 | 12 | 0 |

TABLE 5-continued

BSS-8040

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SPSNMHTSG3NAM1 | 05SNX-647/05SNX-646 | C41365 | 605 | 6 | 28 | 8.5 | 18 | 5 | | 3 |
| 06SPSNMHTBR3NAPL | 05SNX-647/05SNX-646 | C41365 | 605 | 6.5 | 24 | 8 | 17.2 | 9 | | 1 |
| 06SPSNMHTSG2NAM1 | 05SNX-647/05SNX-646 | C41365 | 605 | 7.5 | 30 | 7.5 | 16.4 | 5 | | 0.5 |
| 06SPSNMHTBR5NAPL | 05SNX-647/05SNX-646 | C41365 | 605 | 6.3 | 25 | 8 | 17.6 | 4 | | 0.5 |
| | | | mean | 6.8 | 26.3 | 8.2 | 17.5 | 4.4 | 11.5 | 0.6 |
| | | | stdev | 1.0 | 4.7 | 0.4 | 0.9 | 2.8 | 0.7 | 0.9 |

TABLE 6

GSS-1108

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SPSNMHTBR5NAPL | 05NXB-1497-1BX/05NXB-1496 | C48039 | 605 | 8 | 28 | 8 | 16.8 | 7 | | 0 |
| 06SPSNMHTFIFID2 | 05NXB-1497-1BX/05NXB-1496 | C48039 | 605 | 5 | 22 | 8.3 | 18 | 7 | | 0 |
| 06SPSNMHTSG3NAM1 | 05NXB-1497-1BX/05NXB-1496 | C48039 | 605 | 7.5 | 24 | 8 | 16.8 | 9 | | 0.2 |
| 06SUSNMHTUWLID2 | 05NXB-1497-1BX/05NXB-1496 | C48039 | 605 | 9 | 34 | 7.8 | 16.7 | 1.5 | 10 | 0 |
| 06SPSNMHTBR3NAPL | 05NXB-1497-1BX/05NXB-1496 | C48039 | 605 | 8 | 30 | 7.5 | 16 | 8 | | |
| 06SUSNMHTMHSTAN | 05NXB-1497-1BX/05NXB-1496 | C48039 | 605 | 8.5 | 28 | 8.2 | 19 | 4 | 11 | 0 |
| | | | mean | 7.7 | 27.7 | 8.0 | 17.2 | 6.1 | 10.5 | 0.0 |
| | | | stdev | 1.4 | 4.3 | 0.3 | 1.1 | 2.8 | 0.7 | 0.1 |

TABLE 7

GSS-2128

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SUAMTHTHUEHUOC | 05BXS-5967-1BX/05BXS-5966 | A18604 | 605 | 7.5 | 28 | 7.9 | 15.7 | 2.5 | 11 | 0 |
| 06SUSSTHTMBSTAN | 05BXS-5967-1BX/05BXS-5966 | A18604 | 605 | 8 | 30 | 8.9 | 18.7 | 2.5 | 11 | 0 |
| 05NOSNMHTNMPNAM1 | 03NXB-8273.8271 | A18604 | 605 | 6.5 | 25 | 8.2 | | 2 | 12 | 0.5 |
| 06SPSNMHTSG2NAM1 | 05BXS-5967-1BX/05BXS-5966 | A18604 | 605 | 5.5 | 14 | | | | | |
| 06SUAMTHTHULHUOC | 05BXS-5967-1BX/05BXS-5966 | A18604 | 605 | 6.2 | 35 | 7.9 | 16.7 | 3 | 13 | 0.2 |
| 05WNSNMHTHMRNAPL | 05BXS-5967-1BX/05BXS-5966 | A18604 | 605 | 5 | 16 | 7 | | 8 | | 7 |
| 06SUSNMHTUWLID2 | 05BXS-5967-1BX/05BXS-5966 | A18604 | 605 | 7 | 24 | 8 | 16.7 | 2 | 11 | 0 |
| 06SUSNMHTEL7AUR1 | 05BXS-5967-1BX/05BXS-5966 | A18604 | 605 | 6.6 | 20 | 7.9 | 17.3 | 3 | 13 | 0 |
| 05SUSNMHTNEPNAM1 | 03NXB-8273.8271 | A18604 | 605 | 5.6 | 14 | 8.8 | 16 | 3 | 13 | 0.2 |
| 06SPSNMHTBR3NAPL | 05BXS-5967-1BX/05BXS-5966 | A18604 | 605 | 4 | 26 | 7.5 | 16 | 3 | | 1 |
| 05SUSNMHTNEPNAM1 | 03NXB-8273.8271 | A18604 | 605 | 5.8 | 25 | 8.5 | 17.3 | 4 | 11 | 2 |
| 06SUSNMHTCS6ID2 | 05BXS-5967-1BX/05BXS-5966 | A18604 | 605 | 7.5 | 26 | 7.9 | | 3 | 12 | 0 |
| 06SUSNMHTNMPNAM1 | 05BXS-5967-1BX/05BXS-5966 | A18604 | 605 | | | 9 | 18 | 4 | | 2 |

TABLE 7-continued

GSS-2128

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SPSNMHTFIFID2 | 05BXS-5967-1BX/05BXS-5966 | A18604 | 605 | 5.5 | 18 | 8.2 | 16.4 | 3 | | 0.5 |
| 06SUSNMHTEG1AUR1 | 05BXS-5967-1BX/05BXS-5966 | A18604 | 605 | 7.4 | 30 | 8.3 | 18 | 2 | 11 | 0.5 |
| | | | mean | 6.3 | 23.6 | 8.1 | 17.0 | 3.2 | 11.8 | 1.0 |
| | | | stdev | 1.1 | 6.4 | 0.5 | 1.0 | 1.5 | 0.9 | 1.9 |

TABLE 8

GSS-2305

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SPSNMHTBR5NAPL | 05BX3-8979-1BX/05BX3-8978 | SC8130R | 605 | 6 | 20 | 7.5 | 16.4 | 5 | | 0.5 |
| 06SUAMTHTHUEHUOC | 05BX3-8979-1BX/05BX3-8978 | SC8130R | 605 | 5.6 | 24 | 7.5 | 16.7 | 2 | 11.5 | 0 |
| 06SUAMTHTHULHUOC | 05BX3-8979-1BX/05BX3-8978 | SC8130R | 605 | 5.6 | 20 | 7.1 | 17 | 1 | 12 | 0 |
| 05SUSNMHTNEPNAM1 | 03NX2-9309.9308; | SC8130R | 605 | 6.2 | 25 | 7 | 18.8 | 2.5 | 12 | 0 |
| 06SPSNMHTFIFID2 | 05BX3-8979-1BX/05BX3-8978 | SC8130R | 605 | 5 | 18 | 8 | 16.8 | 2 | | 0 |
| 06SPSNMHTSG3NAM1 | 05BX3-8979-1BX/05BX3-8978 | SC8130R | 605 | 5 | 14 | 7 | 16 | 3 | | |
| 06SUSNMHTEL7AUR1 | 05BX3-8979-1BX/05BX3-8978 | SC8130R | 605 | 6.6 | 28 | 7.5 | 16.7 | 1 | 12 | 0 |
| 06SPSNMHTBR3NAPL | 05BX3-8979-1BX/05BX3-8978 | SC8130R | 605 | 4.8 | 32 | 7.1 | 18.4 | 3 | | |
| 06SUSNMHTEG1AUR1 | 05BX3-8979-1BX/05BX3-8978 | SC8130R | 605 | 7.1 | 20 | 7.5 | 14.7 | 1.5 | 10 | 0 |
| | | | mean | 5.8 | 22.3 | 7.4 | 16.8 | 2.3 | 11.5 | 0.1 |
| | | | stdev | 0.8 | 5.5 | 0.3 | 1.2 | 1.3 | 0.9 | 0.2 |

TABLE 9

GSS-5397

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SUSNMHTEG1AUR1 | 05BXS-5664-1BX/05BXS-5663 | A43252 | 605 | 7.2 | 28 | 7.5 | 17.7 | 3 | 10 | 0.5 |
| 06SUAMTHTHULHUOC | 04BXS-9362.9361 | A43252 | 605 | 5.6 | 20 | 7.5 | 17 | 1.5 | 13 | 0 |
| 06SUAMTHTHUEHUOC | 04BXS-9362.9361 | A43252 | 605 | 7.5 | 24 | 7.5 | 16 | 4 | 10.5 | 1 |
| 06SPSNMHTFIFID2 | 04BXS-9362.9361 | A43252 | 605 | 5 | 14 | 7.8 | 15 | 4 | | 0 |
| 06SUSNMHTEG1AUR1 | 05BXS-5664-1BX/05BXS-5663 | A43252 | 605 | 7.9 | 30 | 7.5 | 16 | 1 | 11 | 0 |
| 06SPSNMHTSG3NAM1 | 04BXS-9362.9361 | A43252 | 605 | 5 | 16 | 7 | 15.6 | 5 | | 0.5 |
| 05NOSNMHTNMPNAM1 | 04BXS-9362.9361 | A43252 | 605 | 6.6 | 27 | 7.7 | | 2 | 12 | 0 |
| 05SUSNMHTNEPNAM1 | 04BXS-9362.9361 | A43252 | 605 | 6 | 20 | 7.9 | 16 | 2.5 | 11 | 0.3 |
| 05SUSNMHTNEPNAM1 | 04BXS-9362.9361 | A43252 | 605 | 6.5 | 30 | 8 | 16.3 | 3 | 10 | 0.2 |
| 06SUSNMHTEL7AUR1 | 04BXS-9362.9361 | A43252 | 605 | 6.9 | 28 | 7.9 | 17.3 | 3 | 11 | 0 |
| 05SUSSTHTMLPSTAN | 04BXS-9362.9361 | A43252 | 605 | | | | | 2 | | 2.5 |
| 06SPSNMHTBR5NAPL | 04BXS-9362.9361 | A43252 | 605 | 5.4 | 16 | 7.1 | 14.4 | 5 | | 0.2 |
| | | | mean | 6.3 | 23.0 | 7.6 | 16.1 | 3.0 | 11.1 | 0.4 |
| | | | stdev | 1.0 | 6.0 | 0.3 | 1.0 | 1.3 | 1.0 | 0.7 |

TABLE 10

GSS-5729

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SUSNMHTUWLID2 | 05BXS-6150-1BX/05BXS-6149 | B32029 | 605 | 8 | 30 | 7.6 | 20 | 1 | 10 | 0 |
| 06SUSNMHTEL7AUR1 | 05BXS-6150-1BX/05BXS-6149 | B32029 | 605 | 7.9 | 28 | 7.9 | 17.7 | 2 | 13 | 0.5 |
| 05NOSNMHTNMPNAM1 | 04CXQ-7290.7289 | B32029 | 605 | | | 8.8 | | 3 | | 0 |
| 06SUSNMHTCS6ID2 | 05BXS-6150-1BX/05BXS-6149 | B32029 | 605 | 9.5 | 34 | 7.5 | 20 | 3.5 | 11 | 0.5 |
| 06SUSNMHTEG1AUR1 | 05BXS-6150-1BX/05BXS-6149 | B32029 | 605 | 8.4 | 31 | 8.3 | 19 | 1 | 12 | 0.5 |
| 05SUSNMHTNEPNAM1 | 04CXQ-7290.7289 | B32029 | 605 | 7.5 | 34 | 8.8 | 18 | 3 | 11 | 0.5 |
| 06SUAMTHTHULHUOC | 05BXS-6150-1BX/05BXS-6149 | B32029 | 605 | 7.9 | 35 | 8.3 | 17.3 | 1 | 14.5 | 0.2 |
| 06SUAMTHTHUEHUOC | 05BXS-6150-1BX/05BXS-6149 | B32029 | 605 | 8.9 | 39 | 7.9 | 19.3 | 2 | 12 | 1 |
| 06SPSNMHTFIFID2 | 05BXS-6150-1BX/05BXS-6149 | B32029 | 605 | 6.5 | 28 | 8.7 | 18.5 | 3 | | 1.5 |
| 06SUSNMHTMHSTAN | 05BXS-6150-1BX/05BXS-6149 | B32029 | 605 | 8.5 | 32 | 8.2 | 18 | 1.5 | 11 | 1.5 |
| | | | mean | 8.1 | 32.3 | 8.2 | 18.6 | 2.1 | 11.8 | 0.6 |
| | | | stdev | 0.9 | 3.6 | 0.5 | 1.0 | 1.0 | 1.4 | 0.5 |

TABLE 11

GSS-6232

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 05SUSSTTMEPSTAN | 04BXS-9434.9433 | C21202 | 605 | 7.5 | 30 | 8.2 | | 0 | 11 | 0.5 |
| 06SUSSTHTMBSTAN | 05BXS-5256-1BX/05BXS-5255 | C21202 | 605 | 7.5 | 28 | 8.5 | 17 | 0 | 10 | 3.5 |
| 06SUAMTHTHULHUOC | 05BXS-5256-1BX/05BXS-5255 | C21202 | 605 | 6.9 | 31 | 8.1 | 17.3 | 0 | 13 | 0.2 |
| 05NOSNMHTNMPNAM1 | 04BXS-9434.9433 | C21202 | 605 | | | 8.8 | | 1 | | 0.5 |
| 06SUSNMHTUWLID2 | 05BXS-5256-1BX/05BXS-5255 | C21202 | 605 | 7 | 24 | 8.3 | 17.3 | | 11 | 2.5 |
| 06SUAMTHTHUEHUOC | 05BXS-5256-1BX/05BXS-5255 | C21202 | 605 | 7.5 | 28 | 8.1 | 17 | 1.5 | 12.5 | 0 |
| 05SUSNMHTNEPNAM1 | 04BXS-9434.9433 | C21202 | 605 | 5.9 | 22 | 8 | 16.3 | 0 | 12 | 1 |
| 06SUSNMHTNMPNAM1 | 05BXS-5256-1BX/05BXS-5255 | C21202 | 605 | | | 9 | 18.8 | 0 | | 0 |
| 06SUSNMHTEG1AUR1 | 05BXS-5256-1BX/05BXS-5255 | C21202 | 605 | 7.9 | 26 | 8.7 | 16.7 | 0 | 10 | 0.5 |
| 06SUSNMHTCS6ID2 | 05BXS-5256-1BX/05BXS-5255 | C21202 | 605 | 7.5 | 26 | 7.9 | 16 | 1 | 12 | 0.2 |
| 06SUSNMHTEL7AUR1 | 05BXS-5256-1BX/05BXS-5255 | C21202 | 605 | 6.9 | 28 | 8.3 | 16 | 0 | 13 | 0 |
| | | | mean | 7.2 | 27.0 | 8.4 | 16.9 | 0.4 | 11.6 | 0.8 |
| | | | stdev | 0.6 | 2.8 | 0.4 | 0.9 | 0.6 | 1.2 | 1.1 |

TABLE 12

GSS-8542

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 05SUSNMHTNEPNAM1 | 04BXS-9780.9779 | D24924 | 605 | 6 | 24 | 8.2 | 17 | 0 | 12 | 0.5 |
| 05NOSNMHTNMPNAM1 | 04BXS-9780.9779 | D24924 | 605 | 7.1 | 32 | 9.1 | | 0 | 11 | 2 |
| 06SUSNMHTCS6ID2 | 04BXS-9780.9779 | D24924 | 605 | 8 | 30 | 8.3 | 18 | 1.5 | 12 | 0 |
| 06SUSNMHTUWLID2 | 04BXS-9780.9779 | D24924 | 605 | 8 | 28 | 8.5 | 18.7 | −1 | 12 | 1.5 |
| 06SUSSTHTMBSTAN | 04BXS-9780.9779 | D24924 | 605 | 8 | 30 | 8.7 | 17.3 | 0.5 | 12 | 0.3 |
| 06SUSNMHTNMPNAM1 | 04BXS-9780.9779 | D24924 | 605 | | | 8.9 | 18.4 | 0 | | 1.5 |

TABLE 12-continued

GSS-8542

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 05SUSSTTMEPSTAN | 04BXS-9780.9779 | D24924 | 605 | 7 | 22 | 8.9 | | −1 | 11 | 2 |
| | | | mean | 7.35 | 27.67 | 8.66 | 17.88 | 0.00 | 11.67 | 1.11 |
| | | | stdev | 0.81 | 3.88 | 0.34 | 0.72 | 0.87 | 0.52 | 0.83 |

TABLE 13

GSS-8811

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SUSNMHTCS5WA2 | 05BXS-5751-1BX/05BXS-5750 | A24206 | 605 | 9 | 30 | 7.2 | 16.7 | 2.5 | 12 | 0 |
| 05SUSNMHTNEPNAM1 | 04BXS-9800.9799 | A24206 | 605 | 6 | 30 | 8.5 | 16.3 | 3 | 11 | 2 |
| 06SUSNMHTEG1AUR1 | 05BXS-5751-1BX/05BXS-5750 | A24206 | 605 | 8.5 | 28 | 7.9 | 17.7 | 2 | 10 | 0.5 |
| 05NOSNMHTNMPNAM1 | 04BXS-9800.9799 | A24206 | 605 | 8 | 27 | 8.2 | | 1.5 | 12 | 0 |
| 06SUSNMHTHUXHUOC | 05BXS-5751-1BX/05BXS-5750 | A24206 | 605 | 7.9 | 31 | 7.9 | 18.3 | 3 | 11 | 0.2 |
| 06SUSNMHTEL7AUR1 | 05BXS-5751-1BX/05BXS-5750 | A24206 | 605 | 7.9 | 31 | 7.9 | 17.7 | 3 | 11 | 0.5 |
| 06SUAMTHTHUEHUOC | 05BXS-5751-1BX/05BXS-5750 | A24206 | 605 | 9.2 | 43 | 7.7 | 17 | 3 | 11 | 0 |
| 06SUSNMHTUWLID2 | 05BXS-5751-1BX/05BXS-5750 | A24206 | 605 | 8.5 | 28 | 7.3 | 16.7 | 1 | 11 | 1 |
| 06SUSSTHTMBSTAN | 05BXS-5751-1BX/05BXS-5750 | A24206 | 605 | 8.5 | 34 | 7.9 | 18.7 | 2.5 | 11 | 1 |
| 06SUSNMHTNMPNAM1 | 05BXS-5751-1BX/05BXS-5750 | A24206 | 605 | | | | | | | |
| 06SUSNMHTUWLID2 | 05BXS-5751-1BX/05BXS-5750 | A24206 | 605 | 8 | 34 | 7.1 | 19.3 | 1 | 12 | 2.5 |
| 06SUSNMHTCS6ID2 | 05BXS-5751-1BX/05BXS-5750 | A24206 | 605 | 9 | 34 | 7.9 | 18.7 | 4 | 11 | 0.2 |
| 06SPSNMHTUDENAM1 | 05BXS-5751-1BX/05BXS-5750 | A24206 | 605 | | | 8 | 17.3 | 5 | | 1 |
| 06SUAMTHTHULHUOC | 05BXS-5751-1BX/05BXS-5750 | A24206 | 605 | 8.9 | 35 | 8.1 | 17.3 | 3 | 13 | 0 |
| | | | mean | 8.3 | 32.1 | 7.8 | 17.6 | 2.7 | 11.3 | 0.7 |
| | | | stdev | 0.9 | 4.4 | 0.4 | 0.9 | 1.1 | 0.8 | 0.8 |

TABLE 14

GSS-8812

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 05NOSNMHTNMPNAM1 | N05CXL-9692.9691 | A24209 | 605 | | | 8 | | 3 | | 0 |
| 07SPSNMHTB52NAPL | N05CXL-9692.9691 | A24209 | 605 | 6.5 | | 7.2 | 16 | 7 | | 1.5 |
| 07SPSNMHTB51NAPL | N05CXL-9692.9691 | A24209 | 605 | 3.5 | | 7.1 | 16 | 7 | | 3 |
| 06SUSNMMTIM6NAM1 | N05CXL-9692.9691 | A24209 | 605 | | | 9 | | 0.1 | | |
| 05SUSNMHTNEPNAM1 | 04BXS-9802.9801 | A24209 | 605 | 6.5 | 34 | 8.4 | 16 | 3 | 12 | 0.3 |
| 06SUAMTHTHULHUOC | N05CXL-9692.9691 | A24209 | 605 | 7.5 | 31 | 8.3 | 17 | 2.5 | 13 | 0 |
| 06SUSNMMTIM6NAM1 | N05CXL-9692.9691 | A24209 | 605 | | | 9.2 | | 0.2 | | 1 |
| 06SUSNMMTIM6NAM1 | N05CXL-9692.9691 | A24209 | 605 | | | 10 | | | | 0.5 |
| 06SUAMTHTHUEHUOC | N05CXL-9692.9691 | A24209 | 605 | 8.9 | 4 | 8.3 | 15.3 | 3 | 11 | 0.2 |
| 06SUSNMHTEG1AUR1 | N05CXL-9692.9691 | A24209 | 605 | 7.9 | 33 | 7.9 | 16.7 | 2 | 9 | 0 |
| 06SUSNMMTIM6NAM1 | N05CXL-9692.9691 | A24209 | 605 | | | 9 | | | 12 | |
| 06SUSNMHTUWLID2 | N05CXL-9692.9691 | A24209 | 605 | 8 | 28 | 8.3 | 16 | 1.5 | 13 | 0 |
| 06SUSNMHTEL7AUR1 | N05CXL-9692.9691 | A24209 | 605 | 7.5 | 28 | 7.9 | 14.7 | 2 | 13 | 0 |
| 06SUSNMHTHUXHUOC | N05CXL-9692.9691 | A24209 | 605 | 7.5 | 28 | 7.3 | 15.7 | 2.5 | 12 | 0.3 |
| 06SPSNMHTUDENAM1 | N05CXL-9692.9691 | A24209 | 605 | | | 8 | 14.7 | 2 | | 0.4 |
| 06SUSSTHTMBSTAN | N05CXL-9692.9691 | A24209 | 605 | 8 | 28 | 8.5 | 17.3 | 0 | 13 | 0.3 |

TABLE 14-continued

GSS-8812

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SUSNMHTCS5WA2 | N05CXL-9692.9691 | A24209 | 605 | 9.5 | 30 | 7.2 | 15.3 | 3.5 | 12 | 0 |
| 06SUSNMMTIM6NAM1 | N05CXL-9692.9691 | A24209 | 605 | | | 8.9 | | −1 | 13 | |
| 06SUSNMMTIM6NAM1 | N05CXL-9692.9691 | A24209 | 605 | | | 8.9 | | −1 | 13 | |
| 06SUSNMMTIM6NAM1 | N05CXL-9692.9691 | A24209 | 605 | | | 9 | | 1.2 | | 0.5 |
| 06SUSNMMTIM6NAM1 | N05CXL-9692.9691 | A24209 | 605 | | | 8.5 | | | 13 | 1 |
| 06SUSNMHTUWLID2 | N05CXL-9692.9691 | A24209 | 605 | 7.5 | 32 | 7.8 | 16.7 | 0.5 | 13 | 0 |
| 06SUSNMHTCS6ID2 | N05CXL-9692.9691 | A24209 | 605 | 9 | 34 | 7.8 | 17.3 | 4 | 13 | 0 |
| 06SUSNMMTIM6NAM1 | N05CXL-9692.9691 | A24209 | 605 | | | 9.5 | | 2 | 10 | |
| 06SUSNMMTIM6NAM1 | N05CXL-9692.9691 | A24209 | 605 | | | 9.5 | | | | |
| 06SUSNMMTIM6NAM1 | N05CXL-9692.9691 | A24209 | 605 | | | 9 | | | | |
| | | | mean | 7.5 | 28.2 | 8.4 | 16.1 | 2.1 | 12.2 | 0.5 |
| | | | stdev | 1.5 | 8.4 | 0.8 | 0.9 | 2.1 | 1.2 | 0.7 |

TABLE 15

GSS-1289

| Trial ID | Admnc | female | male | plant height (ft) | Ear height (in) | Ear Length ave. (in) | row # | Husk length (cm) | Kernel depth (mm) | Tip fill (cm) |
|---|---|---|---|---|---|---|---|---|---|---|
| 06SUSNMHTCS6ID2 | 05BXS-5886-1BX/05BXS-5885 | 605 | D07693 | 8.5 | 26 | 7.6 | 18.7 | 3 | 11 | 0 |
| 06SPSNMHTBR3NAPL | 05BXS-5886-1BX/05BXS-5885 | 605 | D07693 | 6 | 22 | 7.5 | 15.6 | 5 | | 1 |
| 06SUSNMHTEL7AUR1 | 05BXS-5886-1BX/05BXS-5885 | 605 | D07693 | 7.5 | 24 | 7.5 | 17.7 | 1 | 11 | 0 |
| 06SPSNMHTSG3NAM1 | 05BXS-5886-1BX/05BXS-5885 | 605 | D07693 | 6 | 16 | 8 | 18.4 | 2 | | 4 |
| 06SPSNMHTFIFID2 | 05BXS-5886-1BX/05BXS-5885 | 605 | D07693 | 6 | 17 | 8.3 | 18.4 | 1.5 | | 0 |
| 06SUAMTHTHUEHUOC | 05BXS-5886-1BX/05BXS-5885 | 605 | D07693 | 8.2 | 35 | 7.9 | 17.3 | 2 | 11 | 0.5 |
| 06SUAMTHTHULHUOC | 05BXS-5886-1BX/05BXS-5885 | 605 | D07693 | 7.2 | 24 | 7.7 | 18.7 | 1.5 | 13 | 0 |
| 06SPSNMHTBR5NAPL | 05BXS-5886-1BX/05BXS-5885 | 605 | D07693 | 8 | 16 | 7 | 18 | 5 | | 2 |
| 05WNSNMHTHMRNAPL | 05BXS-5886-1BX/05BXS-5885 | 605 | D07693 | 6 | 24 | 6.5 | | 6 | | 3 |
| 06SUSNMHTMHSTAN | 05BXS-5886-1BX/05BXS-5885 | 605 | D07693 | 8 | 28 | 8.2 | 18 | 0 | 10 | 0.5 |
| 06SUSNMHTEG1AUR1 | 05BXS-5886-1BX/05BXS-5885 | 605 | D07693 | 7.9 | 20 | 7.5 | 19.7 | 1 | 10 | 1 |
| 06SUSNMHTUWLID2 | 05BXS-5886-1BX/05BXS-5885 | 605 | D07693 | 8.5 | 24 | 7.2 | 18 | | 9 | 2 |
| | | | mean | 7.3 | 23.0 | 7.6 | 18.0 | 2.5 | 10.7 | 1.2 |
| | | | stdev | 1.0 | 5.4 | 0.5 | 1.0 | 2.0 | 1.3 | 1.3 |

The invention also encompasses plants of inbred sweet corn line R605 and parts thereof further comprising one or more specific, single gene traits, which have been introgressed into inbred sweet corn line R605 from another maize line. The single gene traits is transferred into inbred sweet corn line R605 from any type of maize line, such as for example a field corn line, a sweet corn line, a popcorn line, a white corn line or a silage corn line. Preferably, one or more new traits are transferred to inbred sweet corn line R605, or, alternatively, one or more traits of inbred sweet corn line R605 are altered or substituted. The transfer (or introgression) of the trait(s) into inbred sweet corn line R605 is for example achieved by recurrent selection breeding, for example by backcrossing. In this case, inbred sweet corn line R605 (the recurrent parent) is first crossed to a donor inbred (the non-recurrent parent) that carries the appropriate gene(s) for the trait(s) in question. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference).

The laboratory-based techniques described above, in particular RFLP and SSR, are routinely used in such backcrosses to identify the progenies having the highest degree of genetic identity with the recurrent parent. This permits to accelerate the production of inbred maize lines having at least 90%, preferably at least 95%, more preferably at least 99% genetic identity with the recurrent parent, yet more preferably genetically identical to the recurrent parent, except for the trait(s) introgressed from the donor patent. Such determination of genetic identity is based on molecular markers used in the laboratory-based techniques described above. Such molecular markers are for example those described in Boppenmaier, et al., "Comparisons among strains of inbreds for RFLPs", Maize Genetics Cooperative Newsletter (1991) 65, pg. 90, incorporated herein by reference, or those available from the University of Missouri database and the Brookhaven laboratory database (see http://www.agron.missouri.edu, incorporated herein by reference). The last backcross generation is then selfed to give pure breeding progeny for the gene(s) being transferred. The resulting plants have essentially all of the morphological and physiological characteristics of inbred sweet corn line R605, in addition to the single gene trait(s) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

Many traits have been identified that are not regularly selected for in the development of a new inbred but that can be improved by backcrossing techniques. Examples of traits transferred to inbred sweet corn line R605 include, but are not limited to, waxy starch, herbicide tolerance, resistance for bacterial, fungal, or viral disease, insect resistance, enhanced nutritional quality, improved performance in an industrial process, quality and processing traits such as high processing plant recovery, tender kernels, pleasing taste, uniform kernel size and color, attractive husk package and husked ears, ability to ship long distances, ease of mechanical or manual harvest, tipfill, row straight, altered reproductive capability, such as male sterility or male fertility, yield stability and yield enhancement. Other traits transferred to inbred sweet corn line R605 are for the production of commercially valuable enzymes or metabolites in plants of inbred sweet corn line R605. Other traits transferred to inbred sweet corn line R605 are also different endosperm mutations including a sugary trait (su, e.g., su1), a shrunken trait (sh, e.g., sh2), a brittle trait (bt, e.g., bt1 or bt2, not to be confused with the gene for an endoxin from *Bacillus thuringiensis*, described elsewhere herein), or both white or yellow endosperm color.

Traits transferred to sweet corn inbred line R605 are naturally occurring maize traits, such as naturally occurring sweet corn traits, or are transgenic. Transgenes are originally introduced into a donor, non-recurrent parent using genetic engineering and transformation techniques well known in the art. A transgene introgressed into sweet corn inbred line R605 typically comprises a nucleotide sequence whose expression is responsible or contributes to the trait under the control of a promoter appropriate for the expression of the nucleotide sequence at the desired time in the desired tissue or part of the plant. Constitutive or inducible promoters are used. The transgene may also comprise other regulatory elements such as for example translation enhancers or termination signals. In one embodiment, the nucleotide sequence is the coding sequence of a gene and is transcribed and translated into a protein. In another embodiment, the nucleotide sequence encodes an antisense RNA or a sense RNA that is not translated or only partially translated.

Where more than one trait is introgressed into inbred sweet corn line R605, it is preferred that the specific genes are all located at the same genomic locus in the donor, non-recurrent parent, preferably, in the case of transgenes, as part of a single DNA construct integrated into the donor's genome. Alternatively, if the genes are located at different genomic loci in the donor, non-recurrent parent, backcrossing allows to recover all of the morphological and physiological characteristics of inbred sweet corn line R605 in addition to the multiple genes in the resulting sweet corn inbred line.

The genes responsible for a specific, single gene trait are generally inherited through the nucleus. Known exceptions are, e.g. the genes for male sterility, some of which are inherited cytoplasmically, but still act as single gene traits. In one embodiment, a transgene to be introgressed into sweet corn inbred line R605 is integrated into the nuclear genome of the donor, non-recurrent parent. In another embodiment, a transgene to be introgressed into sweet corn inbred line R605 is integrated into the plastid genome of the donor, non-recurrent parent. In one embodiment, a plastid transgene comprises one gene transcribed from a single promoter or two or more genes transcribed from a single promoter.

In one embodiment, a transgene whose expression results or contributes to a desired trait to be transferred to sweet corn inbred line R605 comprises a virus resistance trait such as, for example, a MDMV strain B coat protein gene whose expression confers resistance to mixed infections of maize dwarf mosaic virus and maize chlorotic mottle virus in transgenic maize plants (Murry et al. Biotechnology (1993) 11:1559-64, incorporated herein by reference). In another embodiment, a transgene comprises a gene encoding an insecticidal protein, such as, for example, a crystal protein of *Bacillus thuringiensis* or a vegetative insecticidal protein from *Bacillus cereus*, such as VIP3 (see for example Estruch et al. Nat Biotechnol (1997) 15:137-41, incorporated herein by reference). In one embodiment, an insecticidal gene introduced into inbred sweet corn line R605 is a Cry1Ab gene or a portion thereof, for example introgressed into sweet corn inbred line R605 from a maize line comprising a Bt-11 event as described in U.S. application Ser. No. 09/042,426, incorporated herein by reference, or from a maize line comprising a 176 event as described in Koziel et al. (1993) Biotechnology 11: 194-200, incorporated herein by reference. In yet another embodiment, a transgene introgressed into sweet corn inbred line R605 comprises an herbicide tolerance gene. For example, expression of an altered acetohydroxyacid synthase (AHAS) enzyme confers upon plants tolerance to various imidazolinone or sulfonamide herbicides (U.S. Pat. No. 4,761,373, incorporated herein by reference). In another embodiment, a non-transgenic trait conferring tolerance to imidazolinones is introgressed into sweet corn inbred line R605 (e.g an "IT" or "IR" trait). U.S. Pat. No. 4,975,374, incorporated herein by reference, relates to plant cells and plants containing a gene encoding a mutant glutamine synthetase (GS) resistant to inhibition by herbicides that are known to inhibit GS, e.g. phosphinothricin and methionine sulfoximine. Also, expression of a Streptomyces bar gene encoding a phosphinothricin acetyl transferase in maize plants results in tolerance to the herbicide phosphinothricin or glufosinate (U.S. Pat. No. 5,489,520, incorporated herein by reference). U.S. Pat. No. 5,013,659, incorporated herein by reference, is directed to plants that express a mutant acetolactate synthase (ALS) that renders the plants resistant to inhibition by sulfonylurea herbicides. U.S. Pat. No. 5,162,602, incorporated herein by reference, discloses plants tolerant to inhibition by cyclohexanedione and aryloxyphenoxypropanoic acid herbicides, such as e.g. Sethoxydim or any herbicidally effective forms of 2-[1-ethoxyimino)butyl]-5-(2-(ethylthio)propyl]-3-hydroxy-2-cyclohexen-1-one, its salts and derivatives. The tolerance is conferred by an altered acetyl coenzyme A carboxylase (ACCase). U.S. Pat. No. 5,554,798, incorporated herein by reference, discloses transgenic glyphosate tolerant maize plants, which tolerance is conferred by an altered 5-enolpyruvyl-3-phosphoshikimate (EPSP) synthase gene. Also, tolerance to a protoporphyrinogen oxidase inhibitor is achieved by expression of a tolerant protoporphyrinogen oxidase enzyme in plants (U.S. Pat. No. 5,767,373, incorporated herein by reference).

In one embodiment, a transgene introgressed into sweet corn inbred line R605 comprises a gene conferring tolerance to a herbicide and at least another nucleotide sequence encoding another trait, such as for example, an insecticidal protein. Such combination of single gene traits is for example a Cry1Ab gene and a bar gene.

Specific transgenic events introgressed into sweet corn inbred line R605 are found at http://www.aphis.usda.gov/bbep/brs/not_reg.html, incorporated herein by reference. These are for example introgressed from glyphosate tolerant event GA21 (application number 9709901p), glyphosate tolerant/Lepidopteran insect resistant event MON 802 (application number 9631701p), Lepidopteran insect resistant event DBT418 (application number 9629101p), male sterile event MS3 (application number 9522801p), Lepidopteran insect resistant event Bt11 (application number 9519501p), phosphinothricin tolerant event B16 (application number 9514501p), Lepidopteran insect resistant event MON 80100 (application number 9509301p), phosphinothricin tolerant events T14, T25 (application number 9435701p), Lepidopteran insect resistant event 176 (application number 9431901p).

The introgression of a Bt11 event into a maize line, such as sweet corn inbred line R605, by backcrossing is exemplified in U.S. application Ser. No. 09/042,426, incorporated herein by reference, and the present invention is directed to methods of introgressing a Bt11 event into sweet corn inbred line R605 using for example the markers described in U.S. application Ser. No. 09/042,426 and to resulting maize lines.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant which do not have the desired herbicide tolerance characteristic, and only those plants which have the herbicide tolerance gene are used in the subsequent backcross. This process is then repeated for the additional backcross generations.

This invention also is directed to methods for producing a maize plant, preferably a sweet corn plant, by crossing a first parent maize plant with a second parent maize plant wherein either the first or second parent maize plant is a sweet corn plant of inbred line R605 or a sweet corn plant of inbred line R605 further comprising one or more single gene traits. Further, both first and second parent maize plants can come from the inbred sweet corn line R605 or an inbred sweet corn plant of R605 further comprising one or more single gene traits. Thus, any such methods using the inbred sweet corn line R605 or an inbred sweet corn plant of R605 further comprising one or more single gene traits are part of this invention: selfing, backcrosses, hybrid production, crosses to populations, and the like. All plants produced using inbred sweet corn line R605 or inbred sweet corn plants of R605 further comprising one or more single gene traits as a parent are within the scope of this invention. Advantageously, inbred sweet corn line R605 or inbred sweet corn plants of R605 further comprising one or more single gene traits are used in crosses with other, different, maize inbreds to produce first generation (F1) maize hybrid seeds and plants with superior characteristics.

In one embodiment, seeds of inbred sweet corn line R605 or seeds of inbred sweet corn plants of R605 further comprising one or more single gene traits are provided as an essentially homogeneous population of inbred corn seeds. Essentially homogeneous populations of inbred seed are those that consist essentially of the particular inbred seed, and are generally purified free from substantial numbers of other seed, so that the inbred seed forms between about 90% and about 100% of the total seed, and preferably, between about 95% and about 100% of the total seed. Most preferably, an essentially homogeneous population of inbred corn seed will contain between about 98.5%, 99%, 99.5% and about 100% of inbred seed, as measured by seed grow outs. The population of inbred corn seeds of the invention is further particularly defined as being essentially free from hybrid seed. Thus, one particular embodiment of this invention is isolated inbred seed of inbred sweet corn plants of R605, e.g. substantially free from hybrid seed or seed of other inbred seed, e.g., a seed lot or unit of inbred seed which is at least 95% homogeneous. The inbred seed population may be separately grown to provide an essentially homogeneous population of plants of inbred sweet corn line R605 or inbred sweet corn plants of R605 further comprising one or more single gene traits.

Seeds of inbred sweet corn plants of R605 for planting purposes is preferably containerized, e.g., placed in a bag or other container for ease of handling and transport and is preferably coated, e.g., with protective agents, e.g., safening or pesticidal agents, in particular antifungal agents and/or insecticidal agents.

When inbred sweet corn line R605 is identified herein, it is understood that the named line include varieties which have the same genotypic and phenotypic characteristics as the identified varieties, i.e., are derived from a common inbred source, even if differently named.

As used herein, the term "plant" includes plant cells, plant protoplasts, plant cell tissue cultures from which maize plants can be regenerated, plant calli, plant clumps, and plant cells that are intact in plants or parts of plants, such as embryos, pollen, ovules, flowers, kernels, ears, cobs, leaves, husks, stalks, roots, root tips, anthers, silk, seeds and the like.

Duncan, Williams, Zehr, and Widholm, Planta (1985) 165: 322-332 reflects that 97% of the plants cultured that produced callus were capable of plant regeneration. Subsequent experiments with both inbreds and hybrids produced 91% regenerable callus that produced plants. In a further study in 1988, Songstad, Duncan & Widholm in Plant Cell Reports (1988), 7:262-265 reports several media additions that enhance regenerability of callus of two inbred lines. Other published reports also indicated that "nontraditional" tissues are capable of producing somatic embryogenesis and plant regeneration. K. P. Rao, et al., Maize Genetics Cooperation Newsletter, 60:64-65 (1986), refers to somatic embryogenesis from glume callus cultures and B. V. Conger, et al., Plant Cell Reports, 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," Maize for Biological Research (Plant Molecular Biology Association, Charlottesville, Va. 1982, at 367-372) and in Duncan, et al., "The Production of Callus Capable of Plant Regeneration from Immature Embryos of Numerous *Zea mays* Genotypes," 165 Planta 322-332 (1985). Thus, another aspect of this invention is to provide cells which upon growth and differentiation produce maize plants having the physiological and morphological characteristics of inbred sweet corn line R605. In one embodiment, cells of inbred sweet corn line R605 are transformed genetically, for example with one or more genes described above, for example by using a transformation method described in U.S. application Ser. No. 09/042,426, incorporated herein by reference, and transgenic plants of inbred sweet corn line R605 are obtained and used for the production of hybrid maize plants.

Maize is used as human food, livestock feed, and as raw material in industry. Sweet corn is usually used as fresh produce, canning or freezing, for human consumption. The food uses of maize, in addition to human consumption of maize kernels, also include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry. Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

The seed of inbred sweet corn line R605 or of inbred sweet corn line R605 further comprising one or more single gene traits, the plant produced from the inbred seed, the hybrid maize plant produced from the crossing of the inbred, hybrid seed, and various parts of the hybrid maize plant can be utilized for human food, livestock feed, and as a raw material in industry.

The present invention therefore also discloses an agricultural product comprising a plant of the present invention or derived from a plant of the present invention. The present invention also discloses an industrial product comprising a plant of the present invention or derived from a plant of the present invention. The present invention further discloses methods of producing an agricultural or industrial product comprising planting seeds of the present invention, growing plant from such seeds, harvesting the plants and processing them to obtain an agricultural or industrial product.

DEPOSIT

Applicants have made a deposit of at least 2500 seeds of inbred sweet corn line R605 with the American Type Culture Collection (ATCC), Manassas, Va., 20110-2209 U.S.A., ATCC Deposit No: PTA-8630. This deposit of the inbred sweet corn line R605 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. Seed of inbred sweet corn line R605, representative seed of said inbred sweet corn line having been deposited under ATCC Accession No: PTA-8630.

2. A maize plant, or parts thereof, produced by growing the seed of claim 1.

3. Pollen of the plant of claim 2.

4. An ovule of the plant of claim 2.

5. An ear of the plant of claim 2.

6. A maize plant, or parts thereof, having all the physiological and morphological characteristics of the plant according to claim 2.

7. A male sterile maize plant, or parts thereof, otherwise having all the physiological and morphological characteristics of the plant according to claim 2.

8. A maize plant, or parts thereof, having all the physiological and morphological characteristics of the plant according to claim 2, and further comprising one or more single gene transferred traits.

9. The maize plant according to claim 8, wherein said single gene transferred trait confers upon said maize plant tolerance to an herbicide.

10. The maize plant according to claim 8, wherein said single gene transferred trait comprises a transgene.

11. The maize plant according to claim 10, wherein said transgene comprises a gene conferring upon said maize plant tolerance to an herbicide.

12. The maize plant according to claim 11, wherein said herbicide is glyphosate, gluphosinate, a sulfonylurea or an imidazolinone herbicide, a hydroxyphenylpyruvate dioxygenase inhibitor or a protoporphyrinogen oxidase inhibitor.

13. The maize plant according to claim 10, wherein said transgene comprises a gene conferring upon said maize plant insect resistance, disease resistance or virus resistance.

14. The maize plant according to claim 13, wherein said gene conferring upon said maize plant insect resistance is a *Bacillus thuringiensis* Cry1Ab gene.

15. The maize plant according to claim 14, further comprising a bar gene.

16. The maize plant according to claim 14, wherein said Cry1Ab gene is introgressed into said maize plant from a maize line comprising a Bt-11 event or a 176 event.

17. A tissue culture of regenerable cells of the maize plant according to claim 2, wherein the tissue regenerates plants capable of expressing all the morphological and physiological characteristics of the plant according to claim 2.

18. The tissue culture according to claim 17, the regenerable cells being selected from the group consisting of embryos, meristems, pollen, leaves, anthers, roots, root tips, silk, flowers, kernels, ears, cobs, husks and stalks, and protoplasts or callus obtained therefrom.

19. A maize plant regenerated from the tissue culture of claim 17, capable of expressing all the morphological and physiological characteristics of inbred sweet corn line R605, seed of said inbred line having been deposited under ATCC Accession No: PTA-8630.

20. A method for producing maize seed comprising crossing a first parent maize plant with a second parent maize plant and harvesting the resultant first generation maize seed, wherein said first or second parent maize plant is the maize plant of claim 2.

21. The method according to claim 20, wherein said first parent maize plant is different from said second parent maize plant, and wherein said resultant seed is a first generation (F1) hybrid maize seed.

22. A method for producing maize seed comprising crossing a first parent maize plant with a second parent maize plant and harvesting the resultant first generation maize seed, wherein said first or second parent maize plant is the maize plant of claim 6.

23. The method according to claim 22, wherein said first parent maize plant is different from said second parent maize plant, wherein said resultant seed is a first generation (F1) hybrid maize seed.

24. A method for producing maize seed comprising crossing a first parent maize plant with a second parent maize plant and harvesting the resultant first generation maize seed, wherein said first or second parent maize plant is the maize plant of claim 8.

25. The method according to claim 24, wherein said first parent maize plant is different from said second parent maize plant, wherein said resultant seed is a first generation (F1) hybrid maize seed.

26. A method for obtaining a maize inbred line comprising:
(a) planting a collection of seeds comprising seed of a hybrid, one of whose parents is the plant according to claim 2, or a maize plant having all the physiological and morphological characteristics of the plant according to claim 2, said collection also comprising seed of said inbred line;
(b) growing plants from said collection of seeds;
(c) identifying an inbred plant from said inbred line;
(d) selecting said inbred plant; and
(e) controlling pollination in a manner which preserves the homozygosity of said inbred plant.

27. The method according to claim 26, wherein said one parent has all the physiological and morphological characteristics of inbred sweet corn line R605, seed of said line having been deposited under ATCC Accession No: PTA-8630, and further comprises one or more single gene transferred traits.

28. A method of producing a sweet corn ear comprising growing the plant according to claim 2 to produce an ear, and harvesting said ear.

29. The method according to claim 28, further comprising isolating a kernel from said ear.

30. The method according to claim 29, further comprising processing said kernel to obtain a sweet corn product.

31. The method according to claim 30, wherein said sweet corn product is a canned or a frozen product, or a fresh produce.

32. A method of producing a sweet corn product comprising obtaining an ear of the plant according to claim 2, isolating a kernel from said ear, and processing said kernel to obtain a sweet corn product.

33. The method according to claim 32, wherein said sweet corn product is a canned or a frozen product, or a fresh produce.

* * * * *